(12) United States Patent
Zhang et al.

(10) Patent No.: US 10,058,639 B2
(45) Date of Patent: Aug. 28, 2018

(54) BIORESORBABLE IRON-BASED ALLOY STENT

(71) Applicant: Lifetech Scientific (Shenzhen) Co., Ltd., Shenzhen (CN)

(72) Inventors: Deyuan Zhang, Shenzhen (CN); Hongtao Sun, Shenzhen (CN); Liping Chen, Shenzhen (CN); Haiping Qi, Shenzhen (CN); Wenjiao Lin, Shenzhen (CN); Li Qin, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 4 days.

(21) Appl. No.: 15/032,100

(22) PCT Filed: Oct. 31, 2014

(86) PCT No.: PCT/CN2014/090110
§ 371 (c)(1),
(2) Date: Apr. 26, 2016

(87) PCT Pub. No.: WO2015/062547
PCT Pub. Date: May 7, 2015

(65) Prior Publication Data
US 2016/0263287 A1 Sep. 15, 2016

(30) Foreign Application Priority Data
Oct. 31, 2013 (CN) .......................... 2013 1 0533326

(51) Int. Cl.
*A61L 31/16* (2006.01)
*A61L 33/00* (2006.01)
(Continued)

(52) U.S. Cl.
CPC .............. *A61L 31/10* (2013.01); *A61F 2/915* (2013.01); *A61L 31/022* (2013.01);
(Continued)

(58) Field of Classification Search
CPC .......... A61L 31/02; A61L 31/16; A61L 31/06; A61L 31/14; A61L 31/10; A61L 33/0041;
(Continued)

(56) References Cited

U.S. PATENT DOCUMENTS 7,931,683 B2 * 4/2011 Weber ................... A61L 31/088
623/1.42
8,961,589 B2 * 2/2015 Kleiner ................... A61L 31/10
623/1.42
(Continued)

*Primary Examiner* — Seema Mathew
(74) *Attorney, Agent, or Firm* — Raymond Sun

(57) ABSTRACT

The invention discloses an absorbable iron-based alloy stent, comprising an iron-based alloy substrate and a degradable polyester in contact with the surface of the substrate, in which the degradable polyester has a weight average molecular weight of between 20,000 and 1,000,000 and a polydispersity index of between 1.2 and 30. With the degradable polyester, the iron-based alloy is capable of corroding rapidly and controllably within a predetermined period. Following implantation into the human body, the degradable stent serves as a mechanical support at early stage, then gradually degrading and being metabolized and absorbed by the human body. During the process of degradation, minimal or no solid product is produced. Ultimately, the configuration of the lumen with an implanted stent as well as the systolic and diastolic functions thereof return to their natural states.

18 Claims, 8 Drawing Sheets

(51) Int. Cl.
*A61L 31/08* (2006.01)
*A61F 2/07* (2013.01)
*A61L 31/10* (2006.01)
*A61F 2/915* (2013.01)
*A61L 31/02* (2006.01)
*A61L 31/14* (2006.01)
*A61L 31/06* (2006.01)
*A61L 31/04* (2006.01)

(52) U.S. Cl.
CPC ........... *A61L 31/041* (2013.01); *A61L 31/042* (2013.01); *A61L 31/06* (2013.01); *A61L 31/08* (2013.01); *A61L 31/146* (2013.01); *A61L 31/148* (2013.01); *A61L 31/16* (2013.01); *A61F 2002/91575* (2013.01); *A61F 2210/0004* (2013.01); *A61F 2210/0076* (2013.01); *A61F 2250/0067* (2013.01); *A61L 2300/236* (2013.01); *A61L 2300/416* (2013.01); *A61L 2300/42* (2013.01); *A61L 2300/434* (2013.01); *A61L 2300/604* (2013.01); *A61L 2300/606* (2013.01); *A61L 2400/18* (2013.01); *A61L 2420/06* (2013.01); *A61L 2430/20* (2013.01)

(58) Field of Classification Search
CPC ...... A61L 33/00; A61L 33/0017; A61F 2/915; A61F 2250/0067; A61F 2250/0068
See application file for complete search history.

(56) References Cited

U.S. PATENT DOCUMENTS

| | | | | |
|---|---|---|---|---|
| 9,878,072 | B2* | 1/2018 | Zhang | A61L 31/148 |
| 2003/0004565 | A1* | 1/2003 | Harnek | A61L 17/005 |
| | | | | 623/1.15 |
| 2004/0267349 | A1* | 12/2004 | Richter | A61L 17/145 |
| | | | | 623/1.13 |
| 2005/0261760 | A1* | 11/2005 | Weber | A61L 29/085 |
| | | | | 623/1.38 |
| 2006/0229711 | A1* | 10/2006 | Yan | A61F 2/02 |
| | | | | 623/1.38 |
| 2006/0234070 | A1* | 10/2006 | Bibber | C23C 22/74 |
| | | | | 428/461 |
| 2006/0271168 | A1* | 11/2006 | Kleine | A61F 2/91 |
| | | | | 623/1.38 |
| 2007/0224244 | A1* | 9/2007 | Weber | A61L 27/047 |
| | | | | 424/426 |
| 2007/0270942 | A1* | 11/2007 | Thomas | A61F 2/07 |
| | | | | 623/1.46 |
| 2008/0035243 | A1* | 2/2008 | Breitenkamp | A61L 27/04 |
| | | | | 148/240 |
| 2008/0132995 | A1* | 6/2008 | Burgermeister | A61F 2/915 |
| | | | | 623/1.15 |
| 2008/0214692 | A1* | 9/2008 | Muratoglu | C08J 3/28 |
| | | | | 522/75 |
| 2009/0074838 | A1* | 3/2009 | Sikes | A61K 9/0024 |
| | | | | 424/426 |
| 2009/0281613 | A1* | 11/2009 | Atanasoska | A61F 2/91 |
| | | | | 623/1.15 |
| 2010/0262224 | A1* | 10/2010 | Kleiner | A61L 31/06 |
| | | | | 623/1.15 |
| 2011/0238149 | A1* | 9/2011 | Atanasoska | A61L 31/022 |
| | | | | 623/1.15 |
| 2011/0276124 | A1* | 11/2011 | Doerr | A61F 2/82 |
| | | | | 623/1.15 |
| 2012/0046735 | A1* | 2/2012 | Sill | A61L 27/04 |
| | | | | 623/1.46 |
| 2012/0271396 | A1* | 10/2012 | Zheng | A61F 2/915 |
| | | | | 623/1.2 |
| 2012/0323311 | A1* | 12/2012 | McClain | A61L 31/10 |
| | | | | 623/1.42 |
| 2014/0166473 | A1* | 6/2014 | Lipkin | C23F 13/14 |
| | | | | 204/196.1 |
| 2017/0340780 | A1* | 11/2017 | Chen | A61L 31/022 |

* cited by examiner

Fe Kα1

Fe Kα1

Fe Ka1

Fe Kα1

Fe Kα1

Fe Ka1

BIORESORBABLE IRON-BASED ALLOY STENT

TECHNICAL FIELD

The present invention relates to a biodegradable implantable medical device, and particularly relates to an absorbable iron-based alloy stent capable of degrading rapidly and controllably within a predetermined period.

BACKGROUND ART

At present, the implantable medical devices are usually made from metals and their alloys, ceramics, polymers and the related composite materials, wherein the metal materials are particularly popular because of their superior mechanical properties, such as high strength, and high toughness.

Iron as an important element in the human body, is involved in many biochemical processes, such as oxygen carrying. Easily corrosive pure iron stents each having a shape similar to that of a clinically used metal stent, made by Peuster M et al. through a laser engraving method, were respectively implanted to the descending aortas of 16 New Zealand rabbits. The animal experimental results showed that there was no thrombosis within 6 to 18 months, and also no adverse events occurred. The pathological examination confirmed that there were no inflammation in local blood vessel walls and no obvious proliferation on smooth muscle cells, preliminarily indicating that the degradable iron stent has good application prospects. But the study also found that the corrosion rate of pure iron was relatively slow in vivo environment, thus the corrosion rate needs to be accelerated. Various techniques for improving the corrosion rate of iron have been continuously developed, including alloying and metallurgical vessel changing methods.

The degradable polyester mainly comprises polylactic acid (PLA), polyglycolic acid (PGA) and poly (lactic acid-co-glycolic acid) (PLGA), polycaprolactone (PCL), etc. These polymers have been widely applied to biomedical engineering materials, such as surgical sutures, bone fixation, vascular repair materials and drug controlled release systems, etc. because of their excellent biocompatibility and bioabsorbability. Among them, the Biomatrix drug-eluting stent made by the Biosensor Company takes 316L stainless steel as a substrate, and PLA as a drug carrier for carrying a Biolimus drug, and the polymer coating can completely degrade within 6 to 9 months; a Synergy drug-eluting stent made by Boston Scientific Corporation takes a Pt—Cr alloy as a substrate, and PLGA as a drug carrier for carrying an Everolimus drug, and the polymer coating can completely degrade within 4 months. At present, there are many companies using poly (L-lactic acid) (PLLA) with a slow rate of degradation to make a completely degradable vascular stent with an absorption period of 2 to 3 years. It can be seen from the above examples that different degradable polyesters have different degradation and absorption periods.

It's been reported that if the surface of the iron-based alloy (including pure iron and medical iron-based alloys) stent was coated with a degradable polyester coating, the degradable polyester coating would produce a product with a carboxyl group in the degradation process in the human body, so that the pH value of the local microenvironment around the implantation position dropped to form a local subacid environment, the overpotential of hydrogen evolution reaction on the surface of the iron-based alloy substrate was reduced, and the hydrogen evolution corrosion was produced in the iron-based alloy substrate, thus producing an iron salt as a degradation product. It was reported that the degradable polyester could be used as the coating of the iron-based alloy substrate to speed up the hydrogen evolution corrosion rate of the iron-based alloy substrate, and reduce the toxic reaction of the stent at the initial stage of degradation, thus being favorable for rapid endothelialization of endothelial cells on the surface of the stent. However, the local subacid environment and the hydrogen evolution have not been confirmed in the industry, and the matching between the degradable polymer degradation and the iron substrate corrosion was not involved in the report.

Human vessels belong to an aqueous system, an oxygen-consuming corrosion can be produced in the iron-based alloy in the vessels to generate Fe $(OH)_2$, and Fe $(OH)_2$ which is quickly oxidized to generate a Fe $(OH)_3$ precipitate (as shown in Formulas 1.1 and 1.2) at the same time. And the metabolism of Fe $(OH)_2$ and Fe $(OH)_3$ as water insolubles in the human body are mainly realized by cell phagocytosis, trace Fe ion ionization and other ways, and metabolism and absorption are slowly carried out. At the same time, corrosion products are wrapped around an iron implant to hinder the diffusion of $O_2$ to Fe and reduce the corrosion rate, thus being unfavorable for further metabolism and absorption of iron.

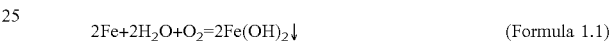

$$2Fe+2H_2O+O_2=2Fe(OH)_2\downarrow \quad \text{(Formula 1.1)}$$

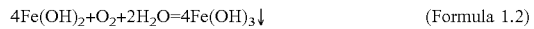

$$4Fe(OH)_2+O_2+2H_2O=4Fe(OH)_3\downarrow \quad \text{(Formula 1.2)}$$

Our early experiments showed that the corrosion rate was greatly reduced after introducing nitrogen and removing oxygen in the corrosion environment. Therefore, we believe that the iron corrosion in the human body is not the hydrogen evolution corrosion as reported, in contrast, the oxygen-consuming corrosion is the most likely or leading reaction.

Our early experiments and theoretical studies also showed that the degradable polyester produced a product with the carboxyl group in the process of degradation, the product with the carboxyl group was coordinated with $Fe^{2+}$ to form a coordination compound, such as ferrous lactate, ferrous acetate and ferrous glycinate (as shown in Formulas 2.1 and 2.2), and such corrosion product was a water soluble iron salt and could be quickly absorbed by the human body. At the same time, the water soluble iron salt could be diffused to other positions of the human body in body fluids, and there was no solid product produced around the iron implant to hinder the direct contact between Fe and $O_2$ so as to accelerate the corrosion of Fe.

$$R_1COOR_2+H_2O=R_1COOH+R_2OH \quad \text{(Formula 2.1)}$$

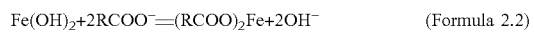

$$Fe(OH)_2+2RCOO^-=(RCOO)_2Fe+2OH^- \quad \text{(Formula 2.2)}$$

The degradable polyester may accelerate the corrosion of the iron-based alloy, and the concentration of iron ions is increased by providing local lactate ions; however, whether the degradation rate of the degradable polyester matches the corrosion rate of the iron-based alloy or not affects the form of the final corrosion product and the iron corrosion period length. Specifically, when the corrosion rate is too fast, the structural integrity and mechanical properties of the implanted iron-based alloy stent at early stage (such as 3 months) will be affected; if the release of iron ions exceeds the absorption power of blood vessels, iron formed by corrosion will be deposited as solid iron rust again in peripheral blood vessels at a certain distance from the implantation position, and remains in the human body for a long time. When the corrosion rate is not enough, the enhancement of the degradable polyester working on the corrosion rate of iron is limited, resulting in a relatively long degradation period of the iron-based alloy stent, for example, for a coronary stent, the stent cannot completely degrade and be absorbed within 1 to 3 years after implantation; for a peripheral vascular stent, the stent cannot completely degrade and be absorbed within 2 to 4 years after implantation yet, which is difficult to highlight the characteristics of degradation and absorption of the iron-based alloy stent. Moreover, whether the corrosion period of the iron-based alloy substrate is matched with the degradation period of the degradable polyester or not also strongly affects the overall degradation period of the iron stent. For example, if the degradable polyester only exists at early stage of corrosion of the iron-based alloy and accelerates the corrosion of the iron-based alloy, after the completion of degradation of the degradable polyester at late stage, the iron-based alloy has not completely corroded, the degradation rate of the remaining iron-based alloy will be relatively slow and the solid iron rust is formed, resulting in the relatively long overall degradation period of the iron-based alloy stent which still cannot meet the clinical time requirement of degradation and absorption of the degradable stent.

Therefore, it is necessary to provide a degradable polyester which can be matched with the iron-based alloy substrate to obtain an absorbable iron-based alloy stent capable of rapidly and controllably degrading within a predetermined period of time.

SUMMARY OF THE INVENTION

An object of the present invention is to select a specific degradable polyester coating to be in contact with the surface of an iron-based alloy substrate or filled inside the iron-based alloy substrate so as to accelerate the corrosion rate of the iron-based alloy substrate in the human body and the controllability of rate and period, and realize the matching between the corrosion rate of the iron-based alloy and the degradation rate of the polyester coating in the whole period, so that the stent not only plays a mechanical support role at early stage but also gradually degrades and is metabolized and absorbed by the human body, and with minimal or no solid product produced from iron corrosion during the absorption process after the implantation of the stent into the human body.

Another object of the present invention is to provide an absorbable iron-based alloy stent comprising the degradable polyester. The iron-based alloy in the iron-based alloy stent can not only rapidly corrode and be absorbed in the human body within a predetermined period of time but also have the mechanical property required by supporting the vessel at early stage of corrosion period under the action of the polyester coating.

Still another object of the present invention is to provide an absorbable iron-based alloy stent comprising the degradable polyester. The iron-based alloy in the iron-based alloy stent can not only rapidly corrode in the human body within a predetermined period of time but also meet the requirements of mechanical properties at early stage and can uniformly corrode within the whole predetermined period of time under the action of the polyester coating, so that the generation rate and the internal absorption rate of a corrosion product of the iron-based alloy substrate are consistent, so that minimal solid product is produced, and the accumulation of the solid product is reduced. Preferably, the iron corrosion product generated can be completely absorbed, so that there is no accumulation.

The term "rapid" means that for an iron-based alloy instrument with an iron-based alloy stent strut of which the thickness is more than or equal to 30 μm and less than 100 μm, the mass loss is more than 10% at three months after the iron-based alloy instrument is implanted into an animal body, and the iron-based alloy completely degrades and is completely absorbed within 1 to 3 years after implantation; for an instrument with an iron-based alloy stent strut of which the thickness is in the range of 100 μm to 300 μm, the mass loss is more than 5% at three month after the iron-based alloy instrument is implanted into the animal body, and the iron-based alloy completely corrodes and degrades and is completely absorbed within 2 to 4 years after implantation.

The term "controllable" means that the rapid corrosion of the iron-based alloy caused by the degradable polyester ensures that the iron-based alloy can maintain sufficient mechanical properties at early stage after the iron-based alloy instrument is implanted into the human body, for example, for the iron-based alloy stent with a stent strut of which the thickness is more than or equal to 30 μm and less than 100 μm, the thickness of the degradable polyester coating is more than or equal to 3 μm and less than or equal to 35 μm, the radial support force is more than 80 kPa at three months after the date of implantation, and the iron-based alloy can completely degrade and be completely absorbed within 2 to 3 years after implantation; for the iron-based alloy stent with a stent strut of which the thickness is in the range of 100 μm to 300 μm, the thickness of the degradable polyester coating is in the range of 10 μm to 60 μm, the radial support force is more than 40 kPa at three months after the date of implantation, and the iron-based alloy can completely degrade and be completely absorbed within 2 to 4 years after implantation.

The term "complete absorption" means that the degradable polyester stent of the present invention (the mass of the corresponding bare iron-based alloy stent is M) is implanted into the animal body, the stent and the vessel into which the stent is implanted are taken out at a predetermined observation point in time, such as 3 months, 6 months, 1 year, 2 years, 3 years or longer, from the date of implantation, and are digested by concentrated nitric acid in a microwave digestion instrument and diluted to $V_0$ with water, and the concentration of iron ions in the diluted solution is $C_0$ by testing; if $$\frac{C_0 \times V_0}{M} \leq 5\%,$$

the stent is considered to be completely absorbed.

The specific conditions for testing the concentration of the iron ions are as follows: the Agilent 240 FS atomic absorption spectrometer is used, the wavelength is 248.3 nm, the slit is 0.2 nm, an oxidant gas is acetylene, and the flow rate is 2.0 L/min.

The degradable polyester is a polymer that contains an ester group —COO— and can degrade in vivo to produce a carboxyl group —COOH. The degradable polyester has a weight average molecular weight in the range of 20,000 to 1,000,000 and a polydispersity index in the range of 1.2 to 30. Furthermore, the weight average molecular weight of the degradable polyester may be more than or equal to 20,000 and less than 50,000, or more than or equal to 50,000 and less than 100,000, or more than or equal to 100,000 and less than 200,000, or more than or equal to 200,000 and less than 300,000, or more than or equal to 300,000 and less than 400,000, or more than or equal to 400,000 and less than 600,000, or more than or equal to 600,000 and less than or equal to 1,000,000 respectively, and the polydispersity index may be more than or equal to 1.2 and less than 5, or more than or equal to 5 and less than 10, or more than or equal to 10 and less than 20, or more than or equal to 20 and less than or equal to 30 respectively.

The numerical interval is in accordance with the mathematical knowledge, namely. [a, b] is more than or equal to a and less than or equal to b; (a, b] is more than a and less than or equal to b; [a, b) is more than or equal to a and less than b. The same applies hereinafter without need of repetition.

On the basis of satisfying the weight average molecular weight range and the polydispersity index range, as an example, the degradable polyester may only be any one from the group consisting of polylactic acid (PLA), polyglycolic acid (PGA), poly(butylene succinate)(PBS) and poly (beta-hydroxy butyrate) (PHB), polycaprolactone (PCL), poly (ethyleneglycol adipate) (PEA), poly(lactic-co-glycolic acid) (PLGA), and poly(3-hydroxybutyrate-co-3-hydroxyvalerate) (PHBV).

As another example, the degradable polyester may also be a mixture of at least two kinds of the same type of degradable polyester polymers with different weight average molecular weights. The "same type" refers to a general term of polymers with the same polymeric monomer (structural unit) and different weight average molecular weights. The above-mentioned mixture may comprise a first kind of degradable polyester polymer with a weight average molecular weight in the range of 20,000 to 50,000 and a second kind of the same type of degradable polyester polymer with a weight average molecular weight in the range of 60,000 to 1,000,000. The second kind of degradable polyester polymer and the first kind of degradable polyester polymer belong to the same type polymer, and the content ratio of the two is in the range of 1:9 to 9:1 in percentage by weight. The degradable polyester may be any one of the following: polylactic acid (PLA), polyglycolic acid (PGA), poly (butylene succinate)(PBS) and poly (beta-hydroxy butyrate) (PHB), polycaprolactone (PCL), poly(ethyleneglycol adipate) (PEA), poly(lactic-co-glycolic acid) (PLGA), and poly(3-hydroxybutyrate-co-3-hydroxyvalerate) (PHBV). As an example, the degradable polyester comprises two kinds of polylactic acids with different weight average molecular weights, the weight average molecular weights of the two kinds of polylactic acids are in the range of 20,000 to 50,000, and in the range of 60,000 to 1,000,000 respectively, and the content ratio of the two is between 1:9 and 9:1.

As another example, the degradable polyester may also be formed by blending at least two of polylactic acid (PLA), polyglycolic acid (PGA), poly(butylene succinate)(PBS) and poly (beta-hydroxy butyrate) (PHB), polycaprolactone (PCL), poly(ethyleneglycol adipate) (PEA), poly(lactic-co-glycolic acid) (PLGA), and poly(3-hydroxybutyrate-co-3-hydroxyvalerate) (PHBV), or formed by copolymerizing monomers of at least two of polylactic acid (PLA), polyglycolic acid (PGA), poly(butylene succinate)(PBS) and poly (beta-hydroxy butyrate) (PHB), polycaprolactone (PCL), poly(ethyleneglycol adipate) (PEA), poly(lactic-co-glycolic acid) (PLGA), and poly(3-hydroxybutyrate-co-3-hydroxyvalerate) (PHBV). As another embodiment embodying the spirit of the present invention, the mixture may comprise polylactic acid (PLA) and poly(lactic-co-glycolic acid) (PLGA), wherein the weight average molecular weight of PLGA is in the range of 20,000 to 300,000, the weight average molecular weight of PLA is in the range of 20,000 to 1,000,000, and the content ratio of the two is in the range of 1:9 to 9:1.

As another example, the degradable polyester may also be a blend comprising polymers with different crystallinities and different degradation periods. As another embodiment embodying the spirit of the present invention, the degradable polyester may be a blend of crystalline and non-crystalline degradable polyester polymers, or a blend of degradable polyester polymers with a high crystallinity and a low crystallinity, wherein the content of polyester with a crystallinity in the range of 5% to 50% is in the range of 10% to 90% in percentage by weight. The degradable polyester may be selected from the group consisting of polylactic acid (PLA), polyglycolic acid (PGA), poly (butylene succinate) (PBS) and poly (beta-hydroxy butyrate) (PHB) . . . polycaprolactone (PCL), poly (ethyleneglycol adipate) (PEA), poly (lactic-co-glycolic acid) (PLGA), and poly (3-hydroxybutyrate-co-3-hydroxyvalerate) (PHBV).

Preferably, the polylactic acid may be poly (DL-lactic acid) or poly (L-lactic acid).

The degradable polyester may also be mixed with an active pharmaceutical ingredient, wherein the active pharmaceutical ingredient may be a vascular proliferation inhibiting drug such as paclitaxel, rapamycin and their derivatives; or an antiplatelet drug selected from cilostazol; or an antithrombotic drug such as heparin; or an anti-inflammatory drug such as dexamethasone. etc, or any drug suitable for being used and compatible with the stent, which is not limited by the present invention; or a mixture of the above-mentioned drugs.

Preferably, the iron-based alloy substrate is selected from pure iron or medical iron-based alloys. Theoretically, at least one of nutrient elements and harmless elements in the human body, or less toxic elements, such as C, N, O, S, P, Mn, Pd, Si, W, Ti, Co, Cr, Cu, and Re may be doped into the pure iron to form a medical iron-based alloy.

The surface of the iron-based alloy substrate is coated with the degradable polyester; or the iron-based alloy substrate is provided with gaps or grooves, and the degradable polyester is embedded in the gaps or grooves; or the iron-based alloy substrate is provided with a cavity, and the degradable polyester is filled in the cavity. Namely, the "surface" of "in contact with the surface of the substrate" not only refers to the outer surface, but also refers to all circumstances in which the degradable polyester or degradable polymer has a contact point or contact surface with the iron-based alloy substrate.

Compared with the prior art, the specific degradable polyester used by the absorbable iron-based alloy stent provided by the present invention can allow the metal substrate of the iron-based alloy to controllably and rapidly corrode within a predetermined period, not only plays a mechanical support role at early stage but also gradually degrades and is metabolized and completely absorbed by the human body within a predetermined period after being implanted into the human body, thus avoiding the long-term risks possibly caused by long-term retention in the human body. And the degradable stent provided by the present invention produces minimal or no solid product from iron corrosion during the absorption process.

BRIEF DESCRIPTION OF THE ACCOMPANYING DRAWINGS

DETAILED DESCRIPTION OF THE EMBODIMENTS

Figure 1:
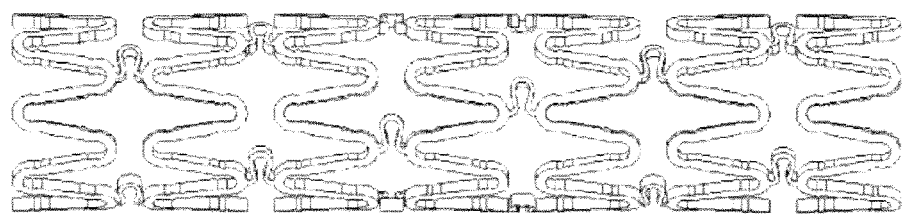
FIG. 1 is a schematic diagram of iron-based alloy stents used by Examples and compared Examples provided by the present invention.

First of all, it is necessary to explain that the effect of a degradable polyester coating in an absorbable iron-based alloy stent on a corrosion of an iron-based alloy substrate was studied in the present invention; namely, after the iron-based alloy stent coated with the degradable polyester was implanted into an animal body, the animal was killed humanely at a predetermined observation point in time, such as 3 months after the date of implantation, then the stent was taken out of the animal body. The radial support force and the weight loss were tested at the corresponding point in time, such as at 3 months, 6 months, 1 year, 2 years, and 3 years, after the date of implantation, and the section of a stent strut of the stent was tested by using an X-ray energy dispersive spectrometer (EDS), and whether a ratio of the mass of iron ions in a solution to the mass of a bare stent (i.e., an iron-based alloy stent uncoated with the degradable polyester) is less than or equal to 5% or not was tested after the stent and the vessel in which the stent was placed were digested to form the solution in order to characterize the rapid and controllable corrosion and complete absorption of the absorbable iron-based alloy stent provided by the present invention during the degradation period. The iron-based alloy substrate is selected from pure iron or medical iron-based alloys. Theoretically, an % of the nutrient elements and harmless elements in the human body, or less toxic elements, such as C, N, O, S, P, Mn, Pd, Si, W, Ti, Co, Cr, Cu, and Re can be doped into the pure iron to form a medical iron-based alloy.

The radial support force can be tested by means of a radial support force tester produced by the MSI Company; namely, the radial support force could be obtained by taking out the stent implanted into the animal body at a predetermined observation point in time together with the blood vessel and directly testing after dewatering and drying.

The weight loss can be tested by the following method: after the vessel in which the stent was implanted into the animal body was cut out at a predetermined observation point in time, the vessel was stripped, the stent was taken out and ultrasonically cleaned in acetonitrile for 20 min, and the degradable polyester coating and its products were removed; then the stent was ultrasonically cleaned in 3% of tartaric acid for at least 20 min, and an iron-based alloy corrosion product adhered onto the surface of the stent was removed; the stent was dried and weighed to obtain the weight of the implanted stent body, and the weight was compared with the weight of the un-implanted original bare stent to obtain a difference value. i.e., the weight loss of the iron-based alloy stent. A percentage of the weight difference value in weight of the original bare stent is usually expressed as the weight loss.

The EDS energy spectrum test was carried out by taking the vessel in which the stent was placed out of the animal body at the predetermined observation point in time, fixing in formalin, processing by dewatering, embedding the blood vessel with methacrylic resin, slicing and polishing along the axial cross section of the stent strut, and putting in a scanning electron microscope after metal spraying for observing and testing, wherein the energy spectrometer is produced by the Oxford Instruments company, and the testing conditions are as follows: the processing time is 5, the spectral range is 0 to 20 KeV, and the channel number is 1 K.

The iron ion concentration test was carried out by taking out the degradable polyester stent (the mass of the bare iron-based alloy stent is M) implanted into the animal body and the vessel in which the stent was placed at the predetermined observation point in time, digesting the stent and the vessel in which the stent was placed in a microwave digestion instrument by using concentrated nitric acid, and testing the concentration $C_0$ of iron ions in a solution under the conditions that the wavelength is 248.3 nm, the slit is 0.2 nm, the oxidants gas is acetylene, and the flow rate is 2.0 L/min by using an Agilent 240 FS atomic absorption spectrometer after diluting with water to form the solution (volume: $V_0$). If $$\frac{C_0 \times V_0}{M} \leq 5\%,$$

the stent is considered to be absorbed completely.

The weight average molecular weight and the polydispersity index of the degradable polyester were tested by using an eight-angle laser light scattering instrument produced by the Wyatt Technology Corporation.

Secondly, the present invention related experiments show that the degradable polyester polymers with different molecular structures have different degradation rates, for example, under the same conditions, the degradation rate of polyglycolic acid (PGA) is greater than that of polylactic acid (PLA); for the same type of degradable polyester polymers, the degradation rate can be affected by the size and distribution of weight average molecular weight and crystallinity. In general, the greater the weight average molecular weight, the slower the degradation rate; the higher the crystallinity, the slower the degradation rate.

The absorbable iron-based alloy stent provided by the present invention comprises an iron-based alloy substrate and a degradable polyester in contact with the surface of the substrate. The degradable polyester for the absorbable iron-based alloy stent provided by the present invention needs to meet the following conditions that: the weight average molecular weight is in the range of 20,000 to 1,000.000 and the polydispersity index is in the range of 1.2 to 30. Furthermore, the weight average molecular weight of the degradable polyester may be more than or equal to 20,000 and less than 50,000, or more than or equal to 50,000 and less than 100,000, or more than or equal to 100,000 and less than 200,000, or more than or equal to 200,000 and less than 300,000, or more than or equal to 300,000 and less than 400,000, or more than or equal to 400,000 and less than 600,000, or more than or equal to 600,000 and less than or equal to 1,000,000 respectively. The polydispersity index may be more than or equal to 1.2 and less than 5, or more than or equal to 5 and less than 10, or more than or equal to 10 and less than 20, or more than or equal to 20 and less than or equal to 30 respectively.

Furthermore, the degradable polyester may only be any one of the followings: polylactic acid (PLA), polyglycolic acid (PGA), poly(butylene succinate)(PBS) and poly (beta-hydroxy butyrate) (PHB), polycaprolactone (PCL), poly (ethyleneglycol adipate) (PEA), poly(lactic-co-glycolic acid) (PLGA), and poly(3-hydroxybutyrate-co-3-hydroxyvalerate) (PHBV).

Alternatively, the degradable polyester polymer may also be a mixture of at least two kinds of the same type of degradable polyester polymers with different weight average molecular weights. For example, the above-mentioned mixture may comprise a first kind of degradable polyester polymer with a weight average molecular weight in the range of 20,000 to 50,000 and a second kind of degradable polyester polymer with a weight average molecular weight in the range of 60,000 to 1,000,000. The second kind of degradable polyester polymer and the first kind of degradable polyester polymer belong to the same type, and the content ratio of the two is in the range of 1:9 to 9:1 in percentage by weight. The degradable polyester polymer may be any one component selected from the group consisting of polylactic acid (PLA), polyglycolic acid (PGA), poly(butylene succinate)(PBS) and poly (beta-hydroxy butyrate) (PHB), polycaprolactone (PCL), poly(ethyleneglycol adipate) (PEA), poly(lactic-co-glycolic acid) (PLGA), and poly(3-hydroxybutyrate-co-3-hydroxyvalerate) (PHBV).

Furthermore, the degradable polyester may also be formed by blending at least two of the followings: polylactic acid (PLA), polyglycolic acid (PGA), poly(butylene succinate)(PBS) and poly (beta-hydroxy butyrate) (PHB), polycaprolactone (PCL), poly(ethyleneglycol adipate) (PEA), poly(lactic-co-glycolic acid) (PLGA), and poly(3-hydroxybutyrate-co-3-hydroxyvalerate) (PHBV), or be formed by copolymerizing monomers of at least two of the followings: polylactic acid (PLA), polyglycolic acid (PGA), poly(butylene succinate)(PBS) and poly (beta-hydroxy butyrate) (PHB), polycaprolactone (PCL), poly(ethyleneglycol adipate) (PEA), poly(lactic-co-glycolic acid) (PLGA), and poly (3-hydroxybutyrate-co-3-hydroxyvalerate) (PHBV). As an example, the mixture may comprise polylactic acid (PLA) and poly (lactic-co-glycolic acid)(PLGA), wherein the weight average molecular weight of PLGA is in the range of 20,000 to 300,000, the weight average molecular weight of PLA is in the range of 20,000 to 1,000,000, and the content ratio of the two is in the range of 1:9 to 9:1 in percentage by weight.

As another example, the degradable polyester may also be a blend comprising polymers with different crystallinities and different degradation periods such as an example, a blend of crystalline and non-crystalline degradable polyester polymers, or a blend of degradable polyester polymers with a high crystallinity and a low crystallinity, in which the content of polyester with a crystallinity in the range of 5% to 50% is in the range of 10% to 90% in percentage by weight. The degradable polyester may be selected from the group consisting of polylactic acid (PLA), polyglycolic acid (PGA), poly(butylene succinate)(PBS) and poly (beta-hydroxy butyrate) (PHB), polycaprolactone (PCL), poly(ethyleneglycol adipate) (PEA), poly(lactic-co-glycolic acid) (PLGA), and poly(3-hydroxybutyrate-co-3-hydroxyvalerate) (PHBV).

The lactic acid above may be poly (DL-lactic acid) or poly (L-lactic acid).

As an application of a drug-eluting stent, the degradable polyester may also be mixed with an active pharmaceutical ingredient, wherein the active pharmaceutical ingredient may be a vascular proliferation inhibiting drug such as paclitaxel, rapamycin and their derivatives, an antiplatelet drug selected from cilostazol, an antithrombotic drug such as heparin, an anti-inflammatory drug such as dexamethasone, or a mixture of the above-mentioned drugs.

The surface of the iron-based alloy substrate may be completely or partially coated with the degradable polyester; or the iron-based alloy substrate is provided with gaps or grooves, and the degradable polyester is embedded in the gaps or grooves; or the iron-based alloy substrate is provided with an inner cavity, and the degradable polyester is filled in the cavity; or a combination of the above-mentioned methods is used.

The absorbable iron-based alloy stent provided by the present invention is further illustrated in conjunction with the following accompanying drawings and examples. It should be especially noted that the iron-based alloy stents adopted by the following examples and control examples have the same shape and size, as shown in FIG. 1. It should be understood that the following examples are only preferred examples of the present invention described herein, but not to limit the present invention. Any modifications, equivalent replacements, improvements. etc. made within the spirit and principles of the present invention should fall in the scope of the present invention described herein.

Example 1

Figure 2:
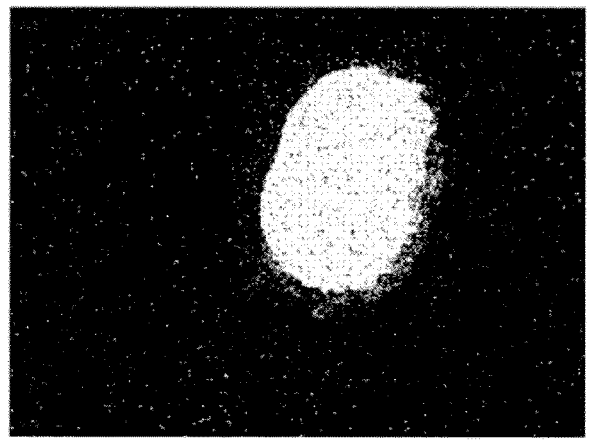
FIG. 2 is an energy spectrum graph of distribution of iron elements on the section of a metal strut at three months after a degradable iron-based alloy stent provided by Example 1 of the present invention is implanted into the abdominal aorta of a rabbit.

The surface of a nitrided pure iron stent with a stent strut of which the thickness is between 60 μm and 70 μm was completely coated with a poly (DL-lactic acid) coating with a thickness of between 8 μm and 15 μm, a weight average molecular weight of 50,000 and a polydispersity index of 2 to obtain an absorbable iron-based alloy stent after drying. The iron-based alloy stent was implanted into the abdominal aorta of a rabbit. The stent was taken out at a corresponding observation point in time, the weight loss percentage and the radial support force of the stent were tested, and the EDS energy spectrum test on the axial cross section of the stent strut was carried out. The test results show that the weight loss of the stent is 25%, the radial support force is 100 kPa, and the EDS energy spectrum test results are shown in FIG. 2 at three months from the date of implantation. It can be seen from FIG. 2 that the corrosion product of the iron stent strut was uniformly distributed in the blood vessel at three months, and no precipitate of solid product was accumulated. The iron ion concentration was 3% by testing after 2.5 years from the date of implantation, indicating that the stent completely degraded and was absorbed.

Example 2

Figure 3:
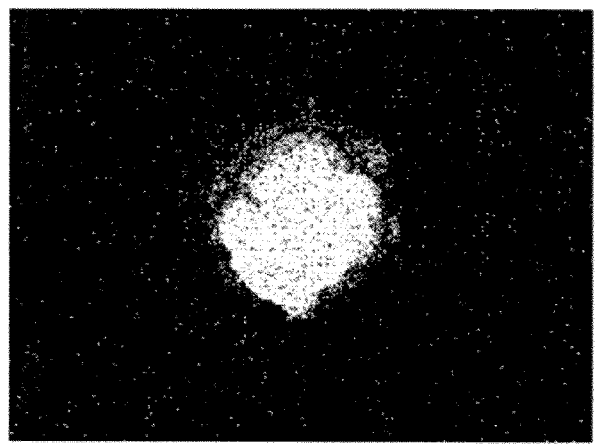
FIG. 3 is an energy spectrum graph of distribution of iron elements on the section of a metal strut at three months after a degradable iron-based alloy stent provided by Example 2 of the present invention is implanted into the abdominal aorta of a rabbit.

The surface of an electrodeposited pure iron (550° C. annealing) stent with a stent strut of which the thickness is between 80 μm and 100 μm was entirely coated with a 15 to 25 μm thick mixture coating of polycaprolactone (PCL) and paclitaxel, wherein the polycaprolactone (PCL) was formed by mixing two kinds of polycaprolactones (PCL) with weight average molecular weights of 20,000 and 80,000 according to a ratio of 1 to 1, the polydispersity index of the mixed polycaprolactones (PCL) was 5, and the mass ratio of polycaprolactones (PCL) to paclitaxel was 2 to 1. An absorbable iron-based alloy stent was obtained after drying. The iron-based alloy stent was implanted into the abdominal aorta of a rabbit. The stent was taken out at a corresponding observation point in time, the weight loss percentage and the radial support force of the stent were tested, and the EDS energy spectrum test on the axial cross section of the stent strut was carried out. The test results show that the weight loss of the stent is 20%, the radial support force is 95 kPa, and the EDS energy spectrum test results are shown in FIG. 3 at three months from the date of implantation. It can be seen from FIG. 3 that the corrosion product of the iron stent strut was uniformly distributed in the blood vessel at three months, and no precipitate of solid product was accumulated. The iron ion concentration was 5% by testing after 2.5 years from the date of implantation, indicating that the stent completely degraded and was absorbed.

Example 3

Figure 4:
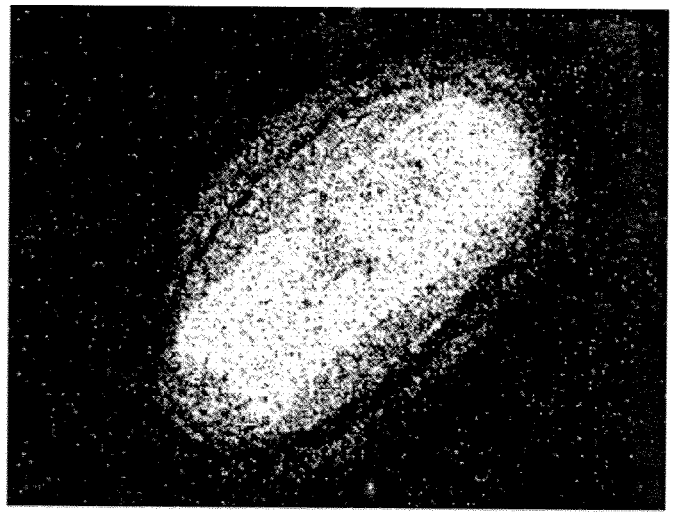
FIG. 4 is an energy spectrum graph of distribution of iron elements on the section of a metal strut at three months after a degradable iron-based alloy stent provided by Example 3 of the present invention is implanted into the abdominal aorta of a rabbit.

The outer wall surface of a nitrided iron stent obtained after heat treatment was coated with a mixture coating of poly (L-lactic acid) and rapamycin by spraying, wherein the mass ratio of the polymer to rapamycin was 2 to 1, the thickness of a stent strut was between 140 μm and 160 μm, and the thickness of the coating was between 30 μm and 40 μm. The poly (L-lactic acid) has an average weight molecular weight of 200,000, a polydispersity index of 4 and a crystallinity of 50%. An absorbable iron-based alloy stent was obtained after drying. The iron-based alloy stent was implanted into the abdominal aorta of a rabbit. The stent was taken out at a corresponding observation point in time, the weight loss percentage and the radial support force of the stent were tested, and the EDS energy spectrum test on the axial cross section of the stent strut was carried out. The test results show that the weight loss of the stent is 8%, the radial support force is 60 kPa, and the EDS energy spectrum test results are shown in FIG. 4 at three months from the date of implantation. It can be seen from FIG. 4 that the corrosion product of the iron stent strut was uniformly distributed in the blood vessel at three months from the date of implantation, and no precipitate of solid product was accumulated. The iron ion concentration was 5% by testing after 3 years from the date of implantation, showing that the stent completely degraded and was absorbed.

Example 4

Figure 5:
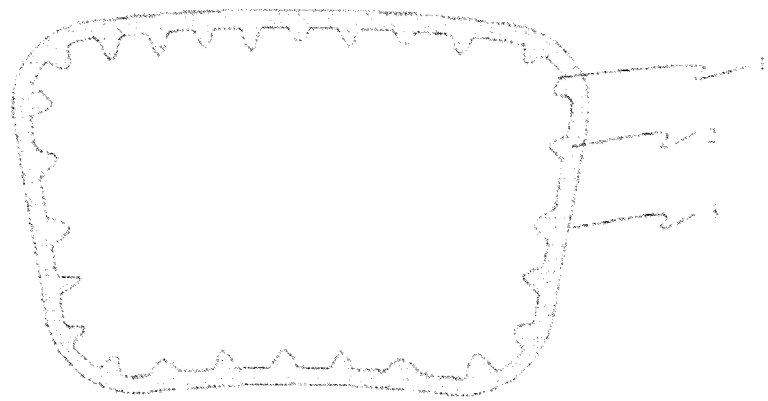
FIG. 5 is a sectional schematic diagram of an iron-based alloy stent coated with the degradable polyester coating provided by Example 4 of the present invention.
Figure 6:
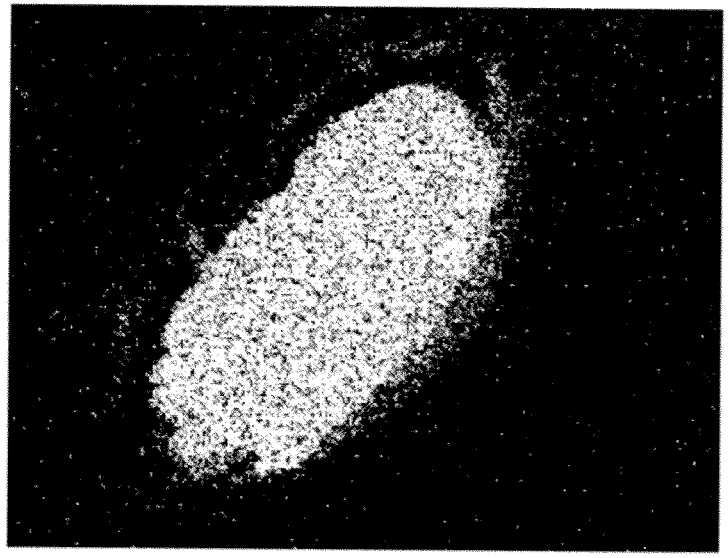
FIG. 6 is an energy spectrum graph of distribution of iron elements on the section of a metal strut at three months after a degradable iron-based alloy stent provided by Example 4 of the present invention is implanted into the abdominal aorta of a rabbit.

A Fe-30Mn-6Si alloy (solid solution treatment) stent was polished so that grooves were distributed in the surface of the stent. As shown in FIG. 5, a stent strut 1 of the stent has a thickness of between 100 μm and 200 μm, and the groove 2 is formed in the surface of the stent strut 1. The surface of the stent strut 1 and the inside of the groove 2 were uniformly coated with a degradable polyester mixture coating 3. The degradable polyester coating was formed by mixing poly (L-lactic acid) with a weight average molecular weight of 70,000 and poly (lactic-co-glycolic acid) with a weight average molecular weight of 30,000 (the molar ratio of lactic acid to glycolic acid was 50 to 50) according to a weight ratio of 1 to 1, the polydispersity index of the mixed poly lactic acid was 5, and the thickness of the mixture coating was between 15 μm and 25 μm. An absorbable iron-based alloy stent was obtained after drying. The iron-based alloy stent was implanted into the abdominal aorta of a rabbit. The stent was taken out at a corresponding observation point in time, the weight loss percentage and the radial support force of the stent were tested, and the EDS energy spectrum test on the axial cross section of the stent strut was carried out. The test results show that the weight loss of the stent is 11%, the radial support force is 80 kPa, and the EDS energy spectrum test results are shown in FIG. 6 at three months from the date of implantation. It can be seen from FIG. 6 that the corrosion product of the iron stent strut was uniformly distributed in the blood vessel at three months from the date of implantation, and no precipitate of solid product was accumulated. The iron ion concentration was 4% by testing after 3 years from the date of implantation, indicating that the stent completely degraded and was absorbed.

Example 5

Figure 7:
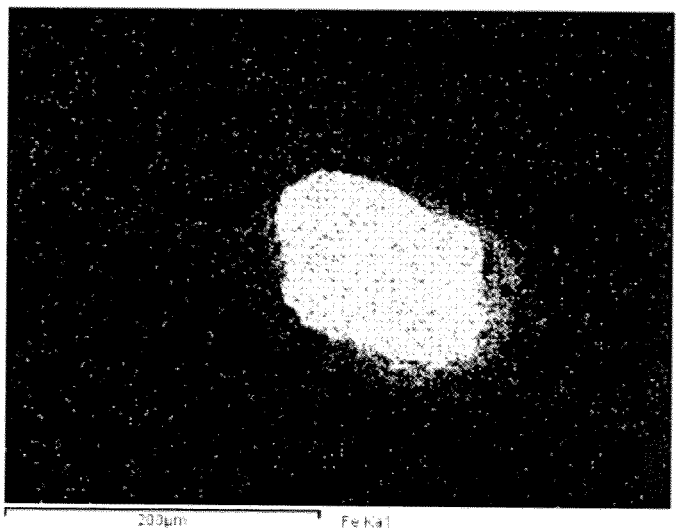
FIG. 7 is an energy spectrum graph of distribution of iron elements on the section of a metal strut at three months after an absorbable iron-based alloy stent provided by Example 5 of the present invention is implanted into the abdominal aorta of a rabbit.

The outer surface of an iron-carbon alloy stent strut with a thickness of between 30 μm and 40 μm, excluding the inner wall of a tubular cavity of a stent, was uniformly coated with a 5 to 8 μm thick PLLA coating with a weight average molecular weight of 20,000 and a polydispersity index of 2. The stent was implanted into the abdominal aorta of a rabbit. The stent was taken out at a corresponding observation point in time, and the weight loss, the radial support force and the EDS test of the stent were tested. The test results show that the weight loss of the stent is 28%, the radial support force is 90 kPa, and the EDS energy spectrum test results are shown in FIG. 7 at three months from the date of implantation. It can be seen from FIG. 7 that the corrosion product of the iron stent strut was uniformly distributed in the blood vessel at three months from the date of implantation, and no precipitate of solid product was accumulated. The iron ion concentration was 2% by testing after 1.5 years from the date of implantation, showing that the stent completely degraded and was absorbed.

Example 6

Figure 8:
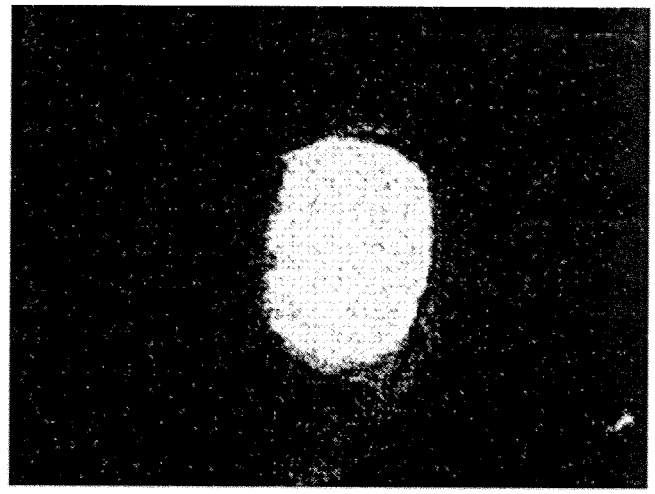
FIG. 8 is an energy spectrum graph of distribution of iron elements on the section of a metal strut at three months after an absorbable iron-based alloy stent provided by Example 6 of the present invention is implanted into the abdominal aorta of a rabbit.

The surface of a sulfurized pure iron stent strut with a thickness of between 240 μm and 260 μm was uniformly coated with a 35 to 55 μm thick coating. The coating comprises two layers, i.e., a PLLA coating with a thickness of between 20 μm and 25 μm as a bottom layer in contact with the stent strut, and a mixed coating of PLGA and heparin according to a ratio of 1 to 1 as a top layer coated on the bottom layer, wherein the PLLA coating has a weight average molecular weight of 100,000 and a polydispersity index of 5 and is at an amorphous state, and the PLGA has a weight average molecular weight of 30,000 and a polydispersity index of 1.8. The stent was implanted into the abdominal aorta of a rabbit. The stent was taken out at a corresponding observation point in time, and the weight loss, the radial support force and the EDS test of the stent were tested. The test results show that the weight loss of the stent is 10%, the radial support force is 50 kPa, and the EDS energy spectrum test results are shown in FIG. 8 at three months from the date of implantation. It can be seen from FIG. 8 that the corrosion product of the iron stent strut was uniformly distributed in the blood vessel at three months from the date of implantation, and no precipitate of solid product was accumulated. The iron ion concentration was 5% by testing after 4 years from the date of implantation, indicating that the stent completely degraded and was absorbed.

Example 7

Figure 9:
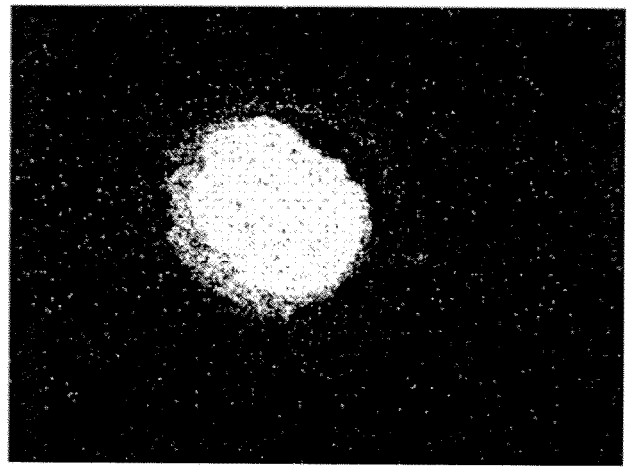
FIG. 9 is an energy spectrum graph of distribution of iron elements on the section of a metal strut at three months after an absorbable iron-based alloy stent provided by Example 7 of the present invention is implanted into the abdominal aorta of a rabbit.

The surface of an iron-manganese alloy stent strut with a thickness of between 120 μm and 150 μm was coated with a 20 to 30 μm thick coating by spraying. The coating was formed by mixing PLGA, PLLA and rapamycin according to a weight ratio of 1 to 9 to 1, wherein the PLLA has a weight average molecular weight of 800,000, a crystallinity of 30%, and a polydispersity index of 2, and the PLGA has a weight average molecular weight of 30,000, a polydispersity index of 3 and a crystallinity of 5%. The stent was implanted into the abdominal aorta of a rabbit. The stent was taken out at a corresponding observation point in time, and then the weight loss, the radial support force and the EDS test of the stent were tested. The test results show that the weight loss of the stent is 8%, the radial support force is 60 kPa, and the EDS energy spectrum test results are shown in FIG. 9 at three months from the date of implantation. It can be seen from FIG. 9 that the corrosion product of the iron stent strut was uniformly distributed in the blood vessel at three months from the date of implantation, and no precipitate of solid product was accumulated. The iron ion concentration was 3% by testing after 3 years from the date of implantation, indicating that the stent completely degraded and was absorbed.

Example 8

Figure 10:
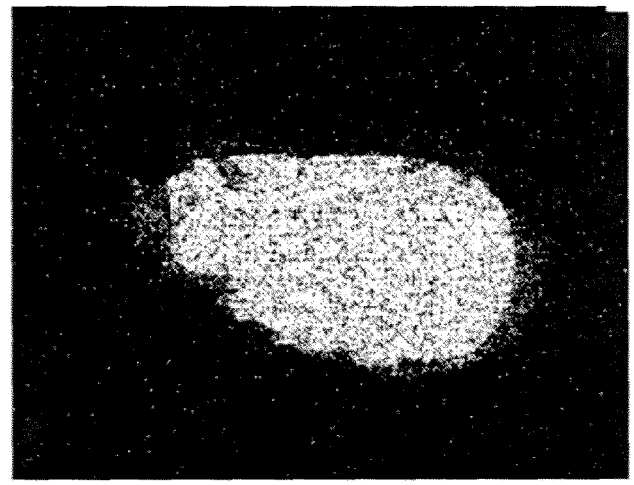
FIG. 10 is an energy spectrum graph of distribution of iron elements on the section of a metal strut the at three months after an absorbable iron-based alloy stent provided by Example 8 of the present invention is implanted into the abdominal aorta of a rabbit.

The surface of a carburized iron stent with a thickness of between 70 μm and 90 μm was coated with a coating with an average thickness of between 10 μm and 20 μm. The coating was formed by mixing poly (DL-lactic acid) (PDLLA) and polyglycolic acid (PGA) according to a weight ratio of 2 to 1, wherein the PDLLA has a weight average molecular weight of 150,000, the PGA has a weight average molecular weight of 50,000, and the polydispersity index after mixing is 10. The stent was implanted into the abdominal aorta of a rabbit, and a sampling test was carried out. The stent was taken out at a corresponding observation point in time, and then the weight loss, the radial support force and the EDS test of the stent were tested. The results show that the weight loss of the stent is 18%, the radial support force is 80 kPa, and the EDS energy spectrum test results are shown in FIG. 10 at three months from the date of implantation. It can be seen from FIG. 10 that the corrosion product of the iron stent strut was uniformly distributed in the blood vessel at three months from the date of implantation, and no precipitate of solid product was accumulated. The iron ion concentration was 4% by testing after 3 years from the date of implantation, indicating that the stent completely degraded and was absorbed.

Example 9

Figure 11:
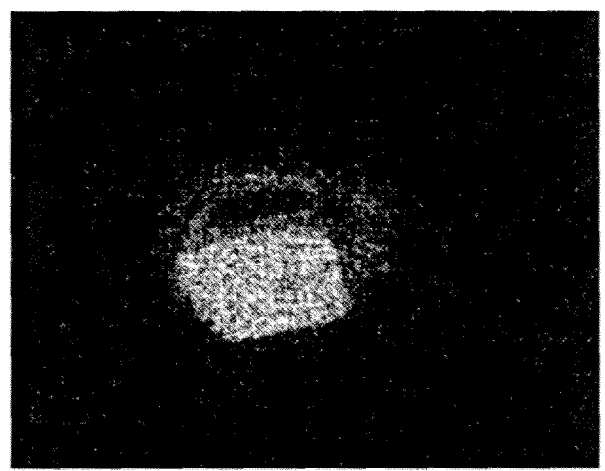
FIG. 11 is an energy spectrum graph of distribution of iron elements on the section of a metal strut at three months after an absorbable iron-based alloy stent provided by Example 9 of the present invention is implanted into the abdominal aorta of a rabbit.

The surface of an iron-cobalt alloy stent with a thickness of between 80 μm and 100 μm was coated with a 20 to 35 μm thick coating. The coating comprises two layers. i.e., a bottom layer and a top layer, wherein polylactic acid (PLA) coating as the bottom layer has a weight average molecular weight of 600,000, a polydipersity index of 7 and a crystallinity of 35%, the top layer is formed by mixing crystalline polylactic acid (PLA), non-crystalline polylactic acid (PLA) and rapamycin according to a ratio of 9 to 1 to 1, and the non-crystalline polylactic acid (PLA) has a weight average molecular weight of 250,000 and a polydispersity index of 1.2. The stent was implanted into the abdominal aorta of a rabbit. A sampling test was carried out at a corresponding observation point in time. The weight loss of the stent is 20%, the radial support force is 85 kPa, and the EDS energy spectrum is shown in FIG. 11 at three months from the date of implantation. It can be seen from Figure that the corrosion product of the stent strut was uniformly distributed in the blood vessel at three months from the date of implantation, and no precipitate of solid product was accumulated. The iron ion concentration was 3% by testing after 2.5 years from the date of implantation, indicating that the stent completely degraded and was absorbed.

Example 10

Figure 12:
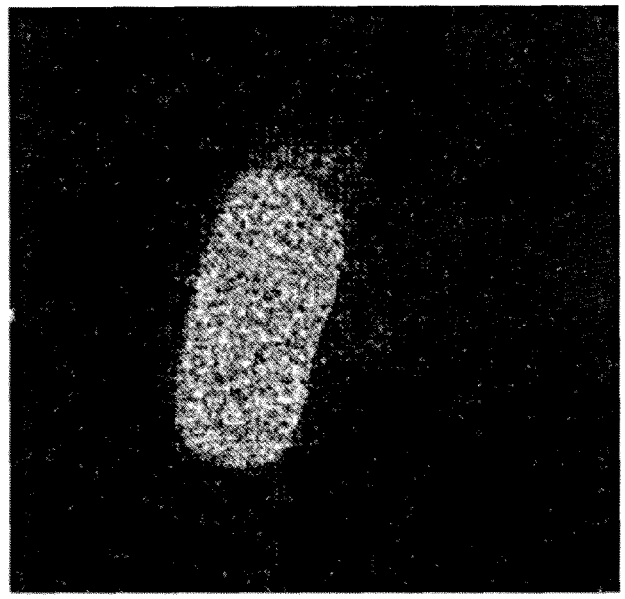
FIG. 12 is an energy spectrum graph of distribution of iron elements on the section of a metal strut at three months after an absorbable iron-based alloy stent provided by Example 10 of the present invention is implanted into the abdominal aorta of a pig.

An iron-palladium alloy stent with a stent strut of which the thickness is between 280 μm and 300 μm was coated with a 30 to 60 μm thick coating. The coating was formed by mixing polylactic acid and polyglycolic acid according to a ratio of 9 to 1, wherein the weight average molecular weight is 400,000 and the polydispersity index is 20 after mixing. The stent was implanted into the abdominal aorta of a pig. A sampling test was carried out at a corresponding observation point in time. The test results show that the radial support force is 45 kPa, the weight loss of the stent is 6%, and the EDS energy spectrum test results are shown in FIG. 12 at three months from the date of implantation. It can be seen from Figure that the stent strut uniformly corroded, and no precipitate of solid product was accumulated. The iron ion concentration was 5% by testing after 4 years from the date of implantation, indicating that the stent completely corroded and was absorbed.

Example 11

Figure 13:
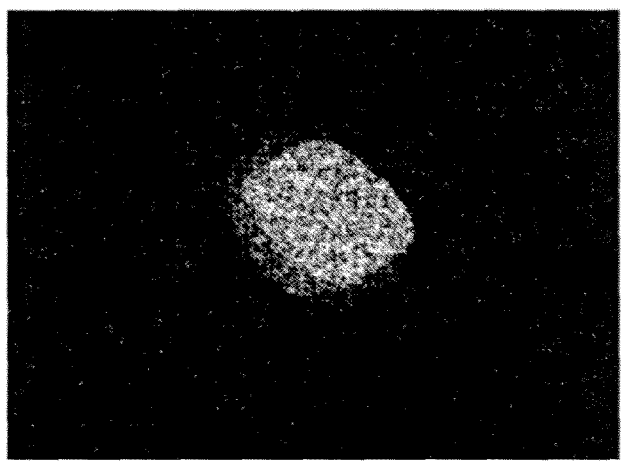
FIG. 13 is an energy spectrum graph of distribution of iron elements on the section of a metal strut at three months after an absorbable iron-based alloy stent provided by Example 11 of the present invention is implanted into the abdominal aorta of a rabbit.

The surface of a pure iron stent with a stent strut of which the thickness is between 40 μm and 50 μm was coated with a 3 to 10 μm thick poly (3-hydroxybutyrate-co-3-hydroxyvalerate) (PHBV) coating. The polymer has a weight average molecular weight of 300,000 and a polydispersity index of 25. The stent was implanted into the abdominal aorta of a rabbit. The stent was respectively taken out at three months and $3^{rd}$ years from the date of implantation to be correspondingly tested. The test results show that the weight loss of the stent is 12%, the radial support force is 80 kPa, and the EDS test results are shown in FIG. 13 at three months from the date of implantation. It can be seen from Figure that the stent strut uniformly corroded, and no precipitate of solid product was accumulated. The iron ion concentration was 4% by testing after 3 years from the date of implantation, indicating that the stent completely corroded and was absorbed.

Example 12

Figure 14:
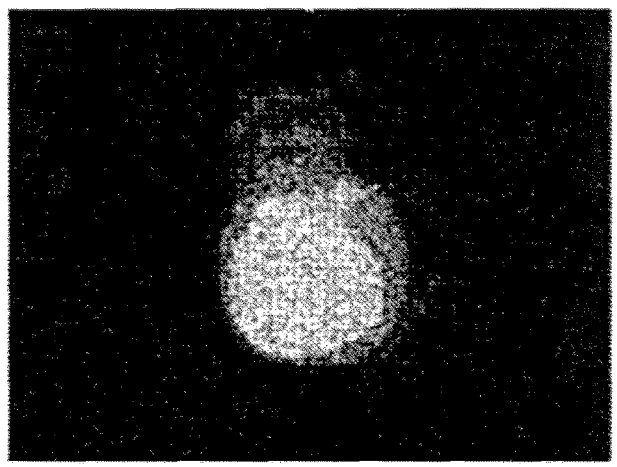
FIG. 14 is an energy spectrum graph of distribution of iron elements on the section of a metal strut at three months after an absorbable iron-based alloy stent provided by Example 12 of the present invention is implanted into the abdominal aorta of a rabbit.

The surface of an iron-nitrogen alloy stent with a stent strut of which the thickness of between 100 μm and 130 μm was coated with a 10 to 20 μm thick poly (DL-lactic acid) coating. The polymer has a weight average molecular weight of 350,000 and a polydispersity index of 15. The stent was implanted into the abdominal aorta of a rabbit. A test was carried out at three months and 3.5 years from the date of implantation, respectively. The test results show that the weight loss of the stent is 9%, the radial support force is 55 kPa, and the EDS energy spectrum test results are shown in FIG. 14 at three months from the date of implantation. It can be seen from Figure that the stent strut uniformly corroded, and no precipitate of solid product was accumulated. The iron ion concentration was 5% by testing after 3.5 years from the date of implantation, indicating that the stent completely corroded.

Example 13

Figure 15:
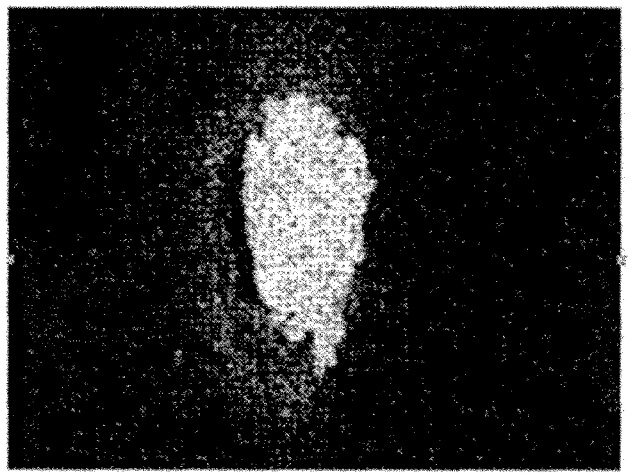
FIG. 15 is an energy spectrum graph of distribution of iron elements on the section of a metal strut at three months after an absorbable iron-based alloy stent provided by Example 13 of the present invention is implanted into the abdominal aorta of a rabbit.

The surface of a pure iron stent with a stent strut of which the thickness is between 120 μm and 150 μm was coated with a 15 to 20 μm thick polylactic acid and polyglycolic acid blend coating. The polylactic acid has a weight average molecular weight of 1,000,000, a crystallinity of 50% and the content of 70%, the polyglycolic acid has a weight average molecular weight of 20,000 and a crystallinity of 15%, and the blend has a polydispersity index of 30. The stent was implanted into the coronary artery of a pig. A corresponding test was carried out at three months and four years from the date of implantation, respectively. The test results show that the weight loss of the stent is 13%, the radial support force is 90 kPa, and the EDS energy spectrum test results are shown in FIG. 15 at three months from the date of implantation. It can be seen from Figure that the stent uniformly corroded, and no precipitate of solid product was accumulated. The iron ion concentration was 4% by testing after 4 years from the date of implantation, indicating that the stent completely corroded.

Compared Example 1

Figure 16:
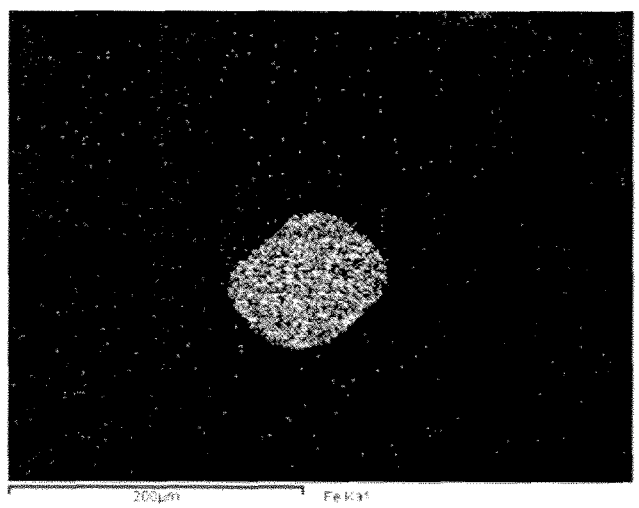
FIG. 16 is an energy spectrum graph of distribution of iron elements on the section of a metal strut at three months after a bare pure iron stent provided by the Control Example 1 of present invention is implanted into the abdominal aorta of a rabbit.

A nitrided pure iron stent (uncoated with any coating on the surface) with a stent strut of which the thickness is between 60 μm and 70 μm was implanted into the abdominal aorta of a rabbit. After 3 months from the date of implantation, the stent was taken out, the weight loss percentage and the radial support force of the stent were tested, and an EDS energy spectrum test on the axial cross section of the stent strut was carried out (see FIG. 16). The test results show that the weight loss of the stent is 5%, and the radial support force is 120 kPa. It can be seen from FIG. 11 that the stent strut remained intact, and almost no corrosion product was produced around the stent strut, indicating that the corrosion rate of the bare pure iron stent was slow. The iron ion concentration test carried out after 3 years from the date of implantation show that the stent is incompletely absorbed.

Compared Example 2

Figure 17:
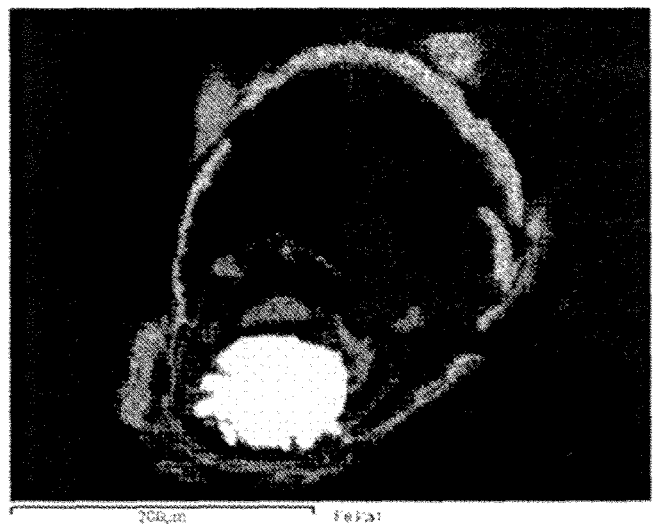
FIG. 17 is an energy spectrum graph of distribution of iron elements on the section of a metal strut at three months after a nitrided iron stent comprising a degradable polyester costing provided by the Control Example 2 of the present invention is implanted into a rabbit body.

The surface of a nitrided pure iron stent with a stent strut of which the thickness is between 60 μm and 70 μm was uniformly coated with a 15 μm thick poly (lactic acid-co-glycolic acid) (the molar ratio of lactic acid to glycolic acid is 50:50). An absorbable iron-based alloy stent was obtained after drying. The poly (lactic acid-co-glycolic acid) has a weight average molecular weight of 15,000 and a polydispersity index of 1.3. The absorbable iron-based alloy stent was implanted into the abdominal aorta of a rabbit. The stent was taken out after 3 months from the date of implantation, the weight loss percentage and the radial support force of the stent were tested, and the EDS energy spectrum test on the axial cross section of the stent strut was carried out (see FIG. 17). The test results show that the weight loss of the stent is 30%, and the radial support force is 60 kPa, indicating that the early corrosion is too rapid, resulting in too rapid decline in early support force, thus being unfavorable for the effective support of the stent on the blood vessel at early stage of implantation. It can be seen from FIG. 12 that because the iron corroded too rapidly at early stage, the release of excessive iron ions was beyond the absorbing capacity of the blood vessel, and a new corrosion product deposition layer was formed around an initial position of the stent strut.

What is claimed is:
1. An absorbable iron-based alloy stent, comprising an iron-based alloy substrate and a degradable polyester coating in contact with the surface of the substrate for accelerating the corrosion rate of the substrate, characterized in that the degradable polyester coating has a weight average molecular weight in the range of 50,000 to 100,000, or 100,000 to 200,000, or 200,000 to 300,000, and a polydispersity index in the range of 1.2 to 5;
  wherein when the thickness of the substrate is more than or equal to 30 μm and less than 100 μm, then the thickness of the degradable polyester coating is in the range of 3 μm to 35 μm, and when the thickness of the substrate is more than or equal to 100 μm to 300 μm, then the thickness of the degradable polyester coating is in the range of 10 μm to 60 μm; and
  wherein the degradable polyester coating is selected from the group consisting of polylactic acid (PLA), polyglycolic acid (PGA), poly(butylene succinate)(PBS) and poly (beta-hydroxy butyrate) (PHB), polycaprolactone (PCL), poly(ethyleneglycol adipate) (PEA), poly(lactic-co-glycolic acid) (PLGA), and poly(3-hydroxybutyrate-co-3-hydroxyvalerate) (PHBV).

2. The absorbable iron-based alloy stent as claimed in claim 1, which is characterized in that the degradable polyester is in contact with the surface of the iron-based alloy substrate by at least one of the following ways: the degradable polyester covers the surface of the iron-based alloy substrate; or the iron-based alloy substrate is provided with gaps or grooves, and the degradable polyester is arranged in the gaps or grooves; or the iron-based alloy substrate is provided with an inner cavity, and the degradable polyester is filled in the inner cavity.

3. The absorbable iron-based alloy stent as claimed in claim 1, which is characterized in that the iron-based alloy substrate is selected from a medical iron-based alloy formed by doping at least one of C, N, O, S, and P into pure iron.

4. The absorbable iron-based alloy stent as claimed in claim 1, which is characterized in that the iron-based alloy substrate is selected from pure iron or a medical iron-based alloy formed by doping at least one of Mn, Pd, Si, W, Ti, Co, Cr, Cu, and Re into pure iron.

5. The absorbable iron-based alloy stent as claimed in claim 1, which is characterized in that the degradable polyester is mixed with an active drug.

6. The absorbable iron-based alloy stent as claimed in claim 1, which is characterized in that the degradable polyester is a polymer which contains an ester group —COO— and is capable of degrading in vivo to produce a carboxyl group —COOH.

7. An absorbable iron-based alloy stent, comprising an iron-based alloy substrate and a degradable polyester coating in contact with the surface of the substrate for accelerating the corrosion rate of the substrate, characterized in that the degradable polyester coating has a polydispersity index in the range of 1.2 to 5;
  wherein when the thickness of the substrate is more than or equal to 30 μm and less than 100 μm, then the thickness of the degradable polyester coating is in the range of 3 μm to 35 μm, and when the thickness of the substrate is more than or equal to 100 μm to 300 μm, then the thickness of the degradable polyester coating is in the range of 10 μm to 60 μm; and
  wherein the degradable polyester comprises at least two kinds of the same type of degradable polyester polymers, wherein the first kind of degradable polyester polymer has a weight average molecular weight in the range of 20,000 to 50,000, the second kind of degradable polyester polymer has a weight average molecular weight in the range of 60,000 to 1,000,000, the ratio of the first degradable polyester polymer to the second degradable polyester polymer is in the range of 1:9 to 9:1 in percentage by weight, and the same type of degradable polyester polymer is any one of the followings: polylactic acid (PLA), polyglycolic acid (PGA), poly(butylene succinate)(PBS) and poly (beta-hydroxy butyrate) (PHB), polycaprolactone (PCL), poly(ethyleneglycol adipate) (PEA), poly(lactic-co-glycolic acid) (PLGA), and poly(3-hydroxybutyrate-co-3-hydroxyvalerate) (PHBV).

8. The absorbable iron-based alloy stent as claimed in claim 7, which is characterized in that the degradable polyester is in contact with the surface of the iron-based alloy substrate by at least one of the following ways: the degradable polyester covers the surface of the iron-based alloy substrate; or the iron-based alloy substrate is provided with gaps or grooves, and the degradable polyester is arranged in the gaps or grooves; or the iron-based alloy substrate is provided with an inner cavity, and the degradable polyester is filled in the inner cavity.

9. The absorbable iron-based alloy stent as claimed in claim 7, which is characterized in that the iron-based alloy substrate is selected from a medical iron-based alloy formed by doping at least one of C, N, O, S, and P into pure iron.

10. The absorbable iron-based alloy stent as claimed in claim 7, which is characterized in that the iron-based alloy substrate is selected from pure iron or a medical iron-based alloy formed by doping at least one of Mn, Pd, Si, W, Ti, Co, Cr, Cu, and Re into pure iron.

11. The absorbable iron-based alloy stent as claimed in claim 7, which is characterized in that the degradable polyester is mixed with an active drug.

12. The absorbable iron-based alloy stent as claimed in claim 7, which is characterized in that the degradable polyester is a polymer which contains an ester group —COO— and is capable of degrading in vivo to produce a carboxyl group —COOH.

13. An absorbable iron-based alloy stent, comprising an iron-based alloy substrate and a degradable polyester coating in contact with the surface of the substrate for accelerating the corrosion rate of the substrate, characterized in that the degradable polyester coating has a weight average molecular weight in the range of 50,000 to 100.000, or 100,000 to 200,000, or 200,000 to 300,000, and a polydispersity index in the range of 1.2 to 5;
  wherein when the thickness of the substrate is more than or equal to 30 μm and less than 100 μm, then the thickness of the degradable polyester coating is in the range of 3 μm to 35 μm, and when the thickness of the substrate is more than or equal to 100 μm to 300 μm, then the thickness of the degradable polyester coating is in the range of 10 μm to 60 μm; and
  wherein the degradable polyester is formed by physically blending at least two of polylactic acid (PLA), polyglycolic acid (PGA), polybutylene succinate)(PBS) and poly (beta-hydroxy butyrate) (PHB), polycaprolactone (PCL), poly(ethyleneglycol adipate) (PEA), poly(lactic-co-glycolic acid) (PLGA), and poly(3-hydroxybutyrate-co-3-hydroxyvalerate) (PHBV), or formed by copolymerizing monomers of at least two of polylactic acid (PLA), polyglycolic acid (PGA), poly(butylene succinate)(PBS) and poly (beta-hydroxy butyrate) (PHB), polycaprolactone (PCL), poly(ethyleneglycol adipate) (PEA), poly(lactic-co-glycolic acid) (PLGA), and poly(3-hydroxybutyrate-co-3-hydroxyvalerate) (PHBV).

14. The absorbable iron-based alloy stent as claimed in claim 13, which is characterized in that the degradable polyester is in contact with the surface of the iron-based alloy substrate by at least one of the following ways; the degradable polyester covers the surface of the iron-based alloy substrate; or the iron-based alloy substrate is provided with gaps or grooves, and the degradable polyester is arranged in the gaps or grooves: or the iron-based alloy substrate is provided with an inner cavity, and the degradable polyester is filled in the inner cavity.

15. The absorbable iron-based alloy stent as claimed in claim 13, which is characterized in that the iron-based alloy substrate is selected from a medical iron-based alloy formed by doping at least one of C, N, O, S, and P into pure iron.

16. The absorbable iron-based alloy stent as claimed in claim 13, which is characterized in that the iron-based alloy substrate is selected from pure iron or a medical iron-based alloy formed by doping at least one of Mn, Pd, Si, W, Ti, Co, Cr, Cu, and Re into pure iron.

17. The absorbable iron-based alloy stent as claimed in claim 13, which is characterized in that the degradable polyester is mixed with an active drug.

18. The absorbable iron-based alloy stent as claimed in claim 13, which is characterized in that the degradable polyester is a polymer which contains an ester group —COO— and is capable of degrading in vivo to produce a carboxyl group —COOH.

\* \* \* \* \*